United States Patent [19]

Sachtler et al.

[11] Patent Number: 4,861,740
[45] Date of Patent: Aug. 29, 1989

[54] MAGNESIUM-EXCHANGED ZEOLITIC CATALYST FOR ISOMERIZATION OF ALKYLAROMATICS

[75] Inventors: J. W. Sachtler, Des Plaines; R. J. Lawson, Palatine, both of Ill.

[73] Assignee: UOP, Des Plaines, Ill.

[21] Appl. No.: 217,505

[22] Filed: Jul. 11, 1988

Related U.S. Application Data

[63] Continuation-in-part of Ser. No. 60,195, Jun. 10, 1987, Pat. No. 4,762,957.

[51] Int. Cl.$^4$ .......................... B01J 29/20; B01J 29/30
[52] U.S. Cl. ....................................... 502/66; 502/61; 502/70; 502/74
[58] Field of Search ........................ 502/66, 74, 78, 61, 502/70; 585/480, 481, 882

[56] References Cited

U.S. PATENT DOCUMENTS

| | | | |
|---|---|---|---|
| 2,403,757 | 7/1946 | Reeves | 585/480 |
| 3,322,690 | 5/1967 | Bilisoly | 502/78 |
| 3,442,966 | 5/1969 | Pollitzer | 502/78 |
| 4,002,578 | 1/1977 | Csicsery | 502/66 |
| 4,121,996 | 10/1978 | Hilfman | 502/66 |
| 4,128,591 | 12/1978 | Carr et al. | 585/482 |
| 4,243,557 | 1/1981 | Gladrow et al. | 502/66 |
| 4,482,773 | 11/1984 | Chu et al. | 585/482 |
| 4,515,902 | 5/1985 | Shioiri et al. | 502/64 |

*Primary Examiner*—Carl F. Dees
*Attorney, Agent, or Firm*—Thomas K. McBride; John F. Spears, Jr.

[57] ABSTRACT

An isomerization catalyst is prepared by a novel method of incorporating magnesium into a crystalline aluminosilicate. The catalyst comprises an alumina matrix, a magnesium-containing zeolite, and a Group VIII metal component. It has been found that the method of magnesium addition can dramatically affect the selectivity to para-xylene, as measured by the loss of $C_8$ aromatics due to undesirable side-reactions during the isomerization of $C_8$ aromatics. The method of the instant invention involves addition of the magnesium to a hydrogel comprising pseudo-boehmite and a zeolite.

21 Claims, 2 Drawing Sheets

MAGNESIUM-EXCHANGED ZEOLITIC CATALYST FOR ISOMERIZATION OF ALKYLAROMATICS

CROSS-REFERENCE TO RELATED APPLICATION

This application is a continuation-in-part of our copending prior application Ser. No. 60,195 filed June 10, 1987. The entire contents of our prior reference are incorporated herein by reference.

FIELD OF THE INVENTION

This invention relates to a catalyst useful for hydrocarbon conversion processes such as the isomerization of disubstituted alkylaromatic hydrocarbons such as xylenes. The invention relates to catalysts and processes with an ability to simultaneously effect the conversion of ethylbenzene or other monosubstituted alkylaromatic hydrocarbons. More specifically, the invention is a catalyst composition consisting essentially of alumina, a Group VIII metal component, and a magnesium form zeolite.

BACKGROUND OF THE INVENTION

Disubstituted alkylaromatic hydrocarbons are useful industrial chemicals. For instance, the xylenes, namely ortho-xylene, meta-xylene and para-xylene, are important chemicals and find wide and varied application in industry. Ortho-xylene is a reactant for the production of phthalic anhydride. Meta-xylene is used in the manufacture of plasticizers, azo dyes, wood preservers, etc. Para-xylene upon oxidation yields terephthalic acid which is used in the manufacture of synthetic textile fibers.

As a result of the important applications to which the individual isomers are subjected, it is often very important to be able to produce high concentrations of a particular isomer. This can be accomplished by converting a non-equilibrium mixture of the isomers, a mixture which is low in the desired isomer, to a mixture which approaches equilibrium concentrations. Various catalysts and processes have been devised to accomplish the isomerization process. For example, it is well known in the art that catalysts such as aluminum chloride, boron fluoride, liquid hydrofluoric acid, and mixtures of hydrofluoric acid and boron fluoride can be used to isomerize xylene mixtures.

Industrially, isomerization of xylenes and conversion of ethylbenzene is one process performed to produce para-xylene. A typical processing scheme for this objective comprises: (a) isomerizing a C$_8$ alkylaromatic mixture to near equilibrium in an isomerization reaction zone; (b) separating out para-xylene using, for example, molecular sieve technology, to obtain a para-xylene rich stream and a stream rich in other xylenes; and, (c) recycling the stream rich in other xylenes to the isomerization reaction zone.

The present invention is particularly concerned with the isomerization reaction step which may be used in an overall process directed to xylene production. An important parameter to consider in this isomerization reaction step is the degree of approach to xylene equilibrium achieved. The approach to equilibrium that is used is an optimized compromise between high C$_8$ aromatic ring loss at high conversion (i.e. very close approach to equilibrium) and high utility costs due to the large recycle rate of unconverted ethylbenzene, ortho-xylene, and meta-xylene. Also contributing to the recycle stream are C$_8$ naphthenes which result from the hydrogenation of ethylbenzene.

It is desirable to run the isomerization process as close to equilibrium as possible in order to maximize the yield of the desired isomer. However, associated with this is a greater cyclic C$_8$ loss due to side-reactions. Cyclic C$_8$ hydrocarbons include xylenes, ethylbenzene, and C$_8$ naphthenes. The correlation of cyclic C$_8$ loss versus the distance from xylene equilibrium is a measure of catalyst selectivity. Thus there is a strong incentive to develop a catalyst formulation which minimizes cyclic C$_8$ loss while maximizing para-xylene yield.

Numerous catalysts have been proposed for use in xylene isomerization processes such as mentioned above. More recently, a number of patents have disclosed the use of crystalline aluminosilicate zeolite-containing catalysts for isomerization and conversion of C$_8$ alkylaromatics. Crystalline aluminosilicates generally referred to as zeolites, may be represented by the empirical formula:

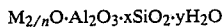

$$M_{2/n}O \cdot Al_2O_3 \cdot xSiO_2 \cdot yH_2O$$

in which n is the valence of M which is generally an element of Group I or II, in particular, sodium, potassium, magnesium, calcium, strontium, or barium, and x is generally equal to or greater than 2. Zeolites have skeletal structures which are made up of three-dimensional networks of SiO$_4$ and AlO$_4$ tetrahedra, corner-linked to each other by shared oxygen atoms. Zeolites with high SiO$_4$/Al$_2$O$_3$ ratio have received much attention as components for isomerization catalysts. Representative of zeolites having such high proportion of SiO$_4$ include mordenite and the ZSM variety.

In addition to the zeolite component, certain metal promoters and inorganic oxide matrices have been included in isomerization catalyst formulations. Examples of such inorganic oxides include silica, alumina, and mixtures thereof. Metal promoters such as Group VIII or Group III metals of the Periodic Table, have been used to provide a dehydrogenation functionality. The acidic function can be supplied by the inorganic oxide matrix, the zeolite, or both.

When employing catalysts containing zeolites for the isomerization of alkylaromatics, characteristics such as acid site strength, zeolite pore diameter, and zeolite surface area become important parameters to consider during formulation development. Variation of these characteristics in a way that reduces side-reactions, such as, transalkylation, is required in order to achieve acceptable levels of cyclic C$_8$ loss.

It has been found that if a catalyst is formulated with the components, and in the manner set forth hereinafter, an improved process for the conversion of a non-equilibrium mixture of xylenes containing ethylbenzene is obtained.

OBJECTS AND EMBODIMENTS

A principal object of the present invention is to provide an improved catalyst for the isomerization of alkylaromatic hydrocarbons with minimal loss of C$_8$ aromatic hydrocarbons. The catalyst of the invention is preferably used in a process for the isomerization of a non-equilibrium feed mixture of xylenes containing ethylbenzene which comprises contacting the feed mixture and hydrogen at isomerization process conditions with a catalyst consisting essentially of an alumina matrix, at least one Group VIII metal component, and 1 to 50 wt. % of a magnesium-containing zeolite prepared as described herein, wherein the zeolite is either mordenite or a pentasil.

The subject invention may also be characterized as a catalyst for the isomerization of a feed stream comprising a non-equilibrium mixture of xylenes containing ethylbenzene, with the catalyst consisting essentially of 75 to 95 wt. % gamma-alumina, 0.1 to 5 wt. % platinum, and 5 to 25 wt. % magnesium-containing mordenite and wherein said catalyst is prepared by (a) contacting a hydrogel comprising pseudo-boehmite and mordenite with an aqueous magnesium solution at a temperature of from 25° to 100° C. for 1 to 24 hours; (b) drying and calcining the resultant hydrogel of step (a) to convert the pseudo-boehmite alumina to essentially gamma-alumina; and, (c) impregnating the calcined hydrogel of step (b) with platinum.

Another embodiment of the invention is a method of manufacturing a hydrocarbon conversion catalyst comprising a zeolite dispersed within a support matrix characterized by the step of contacting an uncalcined hydrogel with an aqueous metal solution at exchange conditions followed by calcination.

INFORMATION DISCLOSURE

The prior art recognizes numerous isomerization processes employing a variety of catalyst formulations. However, it is believed that none of the prior art processes recognizes the use of the catalyst formulation and method of making same which forms an integral part of the instant invention.

U.S. Pat. No. 3,792,100 (Sonoda et al) teaches a process for isomerizing xylenes using a catalyst composition comprising mordenite, which has supported thereon at least one metal selected from the group consisting of copper, silver, and chromium. This reference specifically teaches the removal of alkali or alkaline earth metal ions from the mordenite to allow for the addition of the above-named metals. No reference is made to the utility of either magnesium or a Group VIII metal.

In another reference, U.S. Pat. No. 3,912,659 (Brandenburg et al), a catalyst composite useful for conversion of alkylaromatic hydrocarbons, is disclosed. Specifically, the catalyst is used in a disproportionation process, such as, conversion of toluene into benzene and mixed xylenes. The catalyst comprises a hydrogen form mordenite, an eta or gamma alumina binder, and a sulfided Group VIII metal impregnated on said mordenite. Patentee fails to disclose the utility of a magnesium-containing mordenite.

U.S. Pat. No. 4,159,282 (Olson et al) teaches a process for isomerization of C$_8$ alkylaromatics using a catalyst preferably containing a pentasil zeolite. Reference is made to the possible modification of the zeolite by incorporating therewith an amount of a difficulty reducible oxide, such as, magnesium. However, this reference is silent to the unique combination of a Group VIII metal, magnesium, zeolite, and gamma-alumina as disclosed herein.

A reference similar to the '282 patent is U.S. Pat. No. 4,482,773 (Chu et al) which discloses an isomerization process wherein C$_8$ aromatics are processed over a catalyst comprising HZSM-5, platinum and a Group II-A metal. Magnesium is the preferred Group II-A metal. However, the patent does not teach the use of either mordenite or an alumina matrix. This reference does not appear to discuss adding magnesium to a hydrogel but teaches contacting pure ZSM-5 crystals with an aqueous magnesium solution.

U.S. Pat. No. 4,100,262 (Pelrine) discloses a method of preparation of zeolite ZSM-5 wherein in one embodiment, the patentee teaches that the original cations of the as synthesized ZSM-5 can be replaced with hydrogen, rare earth metals, aluminum, metals of Groups IIA, IIIB, IVB, VIB, VIII, IB, IIB, IIIA, and IVA. Similarly, U.S. Pat. No. 4,218,573 (Tabak et al) discloses a process for isomerizing xylenes wherein the zeolite ZSM-5 used in the catalyst composition may be base exchanged with cations, such as, magnesium. Neither of the two patents recognized the utility of mordenite nor do the references disclose the novel method of preparation of the instant invention.

Other references have discussed the use or production of magnesium-containing catalysts. For instance, U.S. Pat. No. 4,162,214 to G. N. Maslyansky et al. describes a process to produce aromatics including benzene and xylenes from reformates. This reference indicates the catalyst might include a hydrogen-metal-mordenite, with the metal being a rare-earth or alkali-earth metal such as Ca, Mg, Ce, La and mixtures of lanthanides.

U.S. Pat. No. 4,181,811 to L. B. Young presents another example of a zeolitic catalyst which may contain magnesium and which is intended for use with alkylaromatic hydrocarbons. This catalyst, however, apparently does not function as an isomerization catalyst. Rather the catalyst promotes selective cracking and/or transalkylation reactions which consume a 1,4 isomer and produce streams enriched in 1,2 and/or 1,3 isomers.

U.S. Pat. No. 4,128,591 issued to W.E. Carr et al. describes a catalyst for producing a near equilibrium mixture of xylenes from a feed stream of ethylbenzene and mixed xylenes. The catalyst contains a zeolite (mordenite) plus platinum and alumina. The reference teaches a preference to a low level of alkali or alkaline earth metals being present in the mordenite and produces the catalyst by admixing platinum on alumina and mordenite powders. The catalyst is therefore made by a significantly different method which does not include exchanging magnesium into a hydrogel.

DETAILED DESCRIPTION OF THE INVENTION

Figure 1:
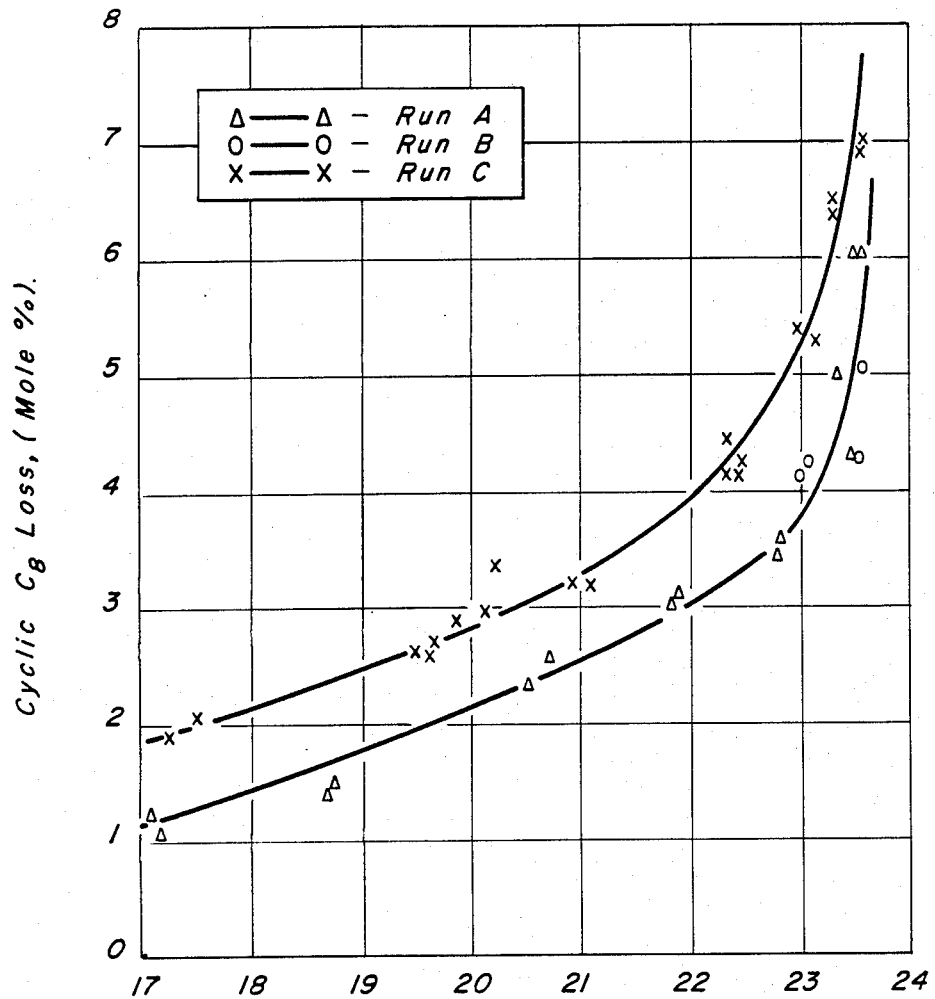
FIG. 1 represents the loss of C$_8$ aromatic hydrocarbons experienced at different levels of paraxylene production for catalysts A and B of the invention and catalyst C, which is a magnesium deficient catalyst.

As mentioned above, this invention is concerned with the manufacture of catalysts for use in hydrocarbon conversion processes. The preferred usage of the subject catalyst is the isomerization of a non-equilibrium mixture of C$_8$ aromatic hydrocarbons. A preferred catalyst of the subject invention consists essentially of alumina, at least one Group VIII metal component, and 1 to 50 wt. % of a magnesium zeolite, wherein the zeolite is either mordenite or a pentasil. The improvement of the instant invention allows for a closer approach to xylene equilibrium resulting in a greater yield of para-xylene without the high loss of C₈ aromatics common to prior art processes.

Those skilled in the art of hydrocarbon conversion processing are aware that the exchange of metals into zeolites may be employed in the manufacture of catalysts useful in a number of hydrocarbon conversion processes such as alkylation, hydrocracking or dehydrogenation. The subject invention is, however, especially applicable to catalysts for the isomerization of isomerizable hydrocarbons including paraffinic hydrocarbons. The preferred usage is the isomerization of alkylaromatic hydrocarbons of the general formula:

$$C_6H_{(6-n)}R_n$$

where n is an integer from 2 to 5 and R is $CH_3$, $C_2H_5$, $C_3H_7$, or $C_4H_9$, in any combination and including all the isomers thereof. The following description of the catalyst and its use will therefore be cast primarily in terms of this one particular usage. Suitable alkylaromatic hydrocarbons include, for example orthoxylene, meta-xylene, para-xylene, ethylbenzene, ethyltoluenes, the trimethylbenzenes, the diethylbenzenes, the triethylbenzenes, methylpropylbenzenes, ethylpropylbenzenes, the diisopropylbenzenes, the triisopropylbenzenes, etc., and mixtures thereof.

It is contemplated that any aromatic C₈ mixture containing ethylbenzene and xylene may be used as feed to such a process. Generally, such a mixture will have an ethylbenzene content in the approximate range of 5 to 50 wt. %, an ortho-xylene content in the approximate range of 0 to 35 wt. %, a meta-xylene content in the approximate range of 20 to 95 wt. % and a para-xylene content in the approximate range of 0 to 15 wt. %. It is preferred that the aforementioned C₈ aromatics comprise a non-equilibrium mixture. The feed to the instant process, in addition to C₈ aromatics, may contain nonaromatic hydrocarbons, i.e. naphthenes and paraffins in an amount up to 30 wt. %.

The alkylaromatic hydrocarbons for isomerization may be utilized as found in selective fractions or various refinery petroleum streams, e.g., as individual components or as certain boiling range fractions obtained by the selective fractionation and distillation of catalytically cracked gas oil. The invention may be utilized for conversion of isomerizable aromatic hydrocarbons when they are present in minor quantities in various streams. The isomerizable aromatic hydrocarbons which may be used in the process of this invention need not be concentrated. The invention allows the isomerization of alkylaromatic containing streams such as reformate to produce specified xylene isomers, particularly para-xylene, thus upgrading the reformate from its gasoline value to a high petrochemical value.

In the preferred use of the present invention an alkylaromatic hydrocarbon charge stock, preferably in admixture with hydrogen, is contacted with the subject catalyst in an alkylaromatic hydrocarbon isomerization zone. Contacting may be effected using the catalyst in a fixed system, a moving bed system, a fluidized bed system, or in a batch-type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phased, or a vapor phase when contacted with the catalyst.

Appropriate hydrocarbon conversion conditions for most reactions are well known in the art. The preferred conditions include a temperature of from 100°-500° C., a pressure of at least one atmosphere and the presence of some vapor within the reaction zone. The isomerizing of an isomerizable hydrocarbon is preferably effected by contacting the hydrocarbon, in a reaction zone containing an isomerization catalyst as hereinafter described, with a fixed catalyst bed by passing the hydrocarbon in a downflow or radial flow fashion through the bed, while maintaining the zone at proper alkylaromatic isomerization conditions such as a temperature in the range from about 100°-600° C. or more, and a pressure of atmospheric to about 100 atmospheres or more. Preferably, the operating temperature ranges from about 300°-500° C. and the pressure ranges from 5-55 atmospheres. The hydrocarbon is preferably, but not necessarily, processed in admixture with hydrogen at a hydrogen to hydrocarbon mole ratio of about 0.5:1 to about 25:1 or more, and at a liquid hourly hydrocarbon space velocity of about 0.1 to about 20 $hr^{-1}$ or more, most preferably at 0.5 to 10 $hr^{-1}$ Other inert diluents such as nitrogen, argon, etc., may be present.

In accordance with the present invention, the catalytic composite comprises an alumina matrix. This matrix is a porous refractory inorganic oxide material having the basic chemical formula of $Al_2O_3$. Suitable alumina materials are the crystalline aluminas known as gamma-, eta-, and theta-alumina, with gamma- or eta-alumina giving best results. In addition, in some embodiments, the alumina carrier material may contain minor proportions, less than 5 wt. percent, of other well known refractory inorganic oxides such as silica, zirconia, magnesia, etc. The preferred support is substantially pure gamma- or eta-alumina. Preferred carrier materials have an apparent bulk density of about 0.3 to about 0.8 g/cc and surface area characteristics such that the average pore diameter is about 20 to 300 angstroms, the pore volume is about 0.1 to about 1 cc/g and the surface area is about 100 to about 500 m²/g. In general, best results are typically obtained with a gamma-alumina carrier material which is used in the form of spherical particles having a relatively small diameter (i.e. typically about 1/16-inch), an apparent bulk density of about 0.3 to about 0.8 g/cc, a pore volume of about 0.7 ml/g, and a surface area of about 150 to about 250 m²/g.

The preferred alumina carrier material may be prepared in any suitable manner and may be synthetically prepared or naturally occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to an aqueous solution of salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention, a particularly preferred form of alumina is the sphere, and alumina spheres may be continuously manufactured by the well-known oil drop method which comprises forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50°–200° C. and subjected to a calcination procedure at a temperature of about 450°–700° C. for a period of about 1 to about 20 hours. This treatment effects conversion of the alumina hydrogel to the corresponding crystalline gamma-alumina. See the teachings of U.S. Pat. No. 2,620,314 for additional details. The manufacture of spheroidal alumina by selective agglomeration is described in U.S. Pat. No. 4,737,478.

An especially preferred method of preparing the alumina matrix involves the inclusion of a zeolite into the alumina hydrosol prior to dropping the hydrosol into an oil bath. This technique yields a hydrogel comprising pseudo-boehmite alumina and zeolite. The amount of zeolite added to the hydrosol can range from 1 to 50 wt. % zeolite based on the weight of the finished catalyst composite. Prior to drying and calcining the resultant hydrogel containing pseudo-boehmite alumina and zeolite, the hydrogel may be subjected to any number of steps to incorporate elements selected from the Group I-A to Group VIII metals. Calcination of the hydrogel transforms the pseudo-boehmite alumina into the more stable and commercially usable gamma-alumina.

The zeolite component of the present invention may be selected from either mordenite or a pentasil. Mordenite is a crystalline aluminosilicate of the zeolite type which is well known to the art as an adsorption agent and as a catalytic agent in hydrocarbon conversion reactions. Mordenite, as typically manufactured or found in nature, is highly siliceous and is characterized by a silica ($SiO_2$) to alumina ($Al_2O_3$) mole ratio of about 10. Two synthetic types of mordenite are available; "large-port" and "small-port" mordenites. Studies of the adsorption behavior of mordenite and the first synthetic types indicated that the pore structure was considerably smaller than the structure indicated. These types are referred to as small-port mordenite; they exhibit an adsorption diameter of about 4 angstroms. By varying synthesis conditions, a large-port mordenite has been synthesized which possesses the adsorption properties expected for the structure. After activation (dehydration), large-port mordenite adsorbs large molecules such as benzene and cyclohexane which are completely excluded by the small-port variety. The large-port mordenite is preferred in the instant invention. The mordenite crystalline structure comprises four- and five-membered rings of $SiO_4$ and $AlO_4$ tetrahedra so arranged that the resulting crystal lattice comprises pores and channels running parallel along the crystal axis to give a tubular configuration. This structure is unique among some zeolite crystalline aluminosilicates in that the channels do not intersect and access to the cages or active sites can be from only one direction. For this reason, the mordenite structure is frequently referred to as two-dimensional in contrast to the other known crystalline aluminosilicates such as faujasite in which the cavities can be entered from three directions.

As stated, mordenite, as commercially available, has an $SiO_2/Al_2O_3$ mole ratio of about 10 and is usually characterized as being in the sodium form. Before the sodium form of mordenite can be utilized as an effective catalyst for hydrocarbon conversion reactions, it must be first converted to the hydrogen form and/or ion exchanged to replace the alkali metal ion (typically sodium) with a desired metal cation. Mordenite, since it has a high initial $SiO_2/Al_2O_3$ mole ratio and is more acid resistant than faujasite, may be converted to the hydrogen form by replacing the sodium ion with a hydrogen ion by treatment with an aqueous solution of a mineral acid. Alternatively, the hydrogen ion can be incorporated by ion exchange with ammonium hydroxide and then calcining the ammonium form mordenite. Hydrogen ion exchanged mordenites are often termed H-mordenite and are illustrated in U.S. Pat. No. 3,281,482. The catalytic activity of mordenites may also be increased by extracting a portion of the alumina from the mordenite crystal structure, as well as simultaneously ion exchanging hydrogen ions, by treatment with mineral acids under relatively severe temperatures and contact time. What is produced are aluminum-deficient mordenites maintaining the same gross crystal structure in terms of gross interatomic distances as the original mordenite, as measured by X-ray diffraction patterns. Mordenites that have been so acid extracted typically have an $SiO_2/Al_2O_3$ ratio in excess of 25:1 which may extend to 100:1 or more. These acid extracted mordenites are exemplified by U.S. Pat. No. 3,480,539. Acid extracted mordenites which are particularly effective and active catalysts have $SiO_2/Al_2O_3$ ratios in excess of 50:1. However, we have found that the use of dealuminated mordenites causes increased loss of $C_8$ cyclics. Although the mechanism is not proven, we speculate that the increased cyclics loss is due to an increase in zeolite pore diameter upon dealumination. This increased pore size reduces steric constraints on the transition state for transalkylation, leading to increased $C_8$ cyclics loss by transalkylation.

It is preferred that sodium cation removal be accomplished by ammonium ion exchange. The $NH_4$-mordenite that results is converted to hydrogen form mordenite during calcination. In the preferred embodiment, this ammonium ion exchange is already achieved to some extent by the treatment of the hydrogel spheres with ammoniacal solutions during aging, and completed during the subsequent washing with 0.5 wt. % $NH_3/H_2O$ solution at 95° C.

Alternatively, the zeolite component of the present invention may be a pentasil crystalline aluminosilicate zeolite. "Pentasil" is a term used to describe a class of shape selective zeolites. This novel class of zeolites is well known to the art and is typically characterized by a silica-to-alumina mole ratio of at least about 12. Suitable descriptions of the pentasils may be found in U.S. Pat. Nos. 4,159,282, 4,163,018, and 4,278,565, all of which are incorporated herein by reference. Of the pentasil zeolites, the preferred ones are ZSM-5, ZSM-8, ZSM-11, ZSM-12, ZSM-23, and ZSM-35, with ZSM-5 being particularly preferred.

It is also within the scope of the present invention that the particular pentasil selected may be a gallosilicate. Gallosilicates have essentially the same structure as the ZSM-type zeolites described hereinabove, except that all or part of the aluminum atoms in the aluminosilicate crystal framework are replaced by gallium atoms. This substitution of the aluminum by gallium is usually performed prior to or during synthesis of the zeolite. The gallium content for this particular type of pentasil, expressed as mole ratios of $SiO_2$ to $Ga_2O_3$, ranges from 20:1 to 400:1 or more.

Regardless of the type of zeolite used, it is desired that the zeolite be predominantly in the sodium form prior to its commingling with the alumina matrix. In a preferred embodiment, the zeolite is commercially obtained in the sodium form and used directly with the alumina hydrosol. The hydrosol is then dispersed into an oil bath as described above to form a hydrogel.

Upon forming the hydrogel containing the pseudo-boehmite alumina and zeolite, the addition of magnesium to zeolite is performed. Although not exactly understood, superior results are obtained, as exemplified in the examples to follow, when the magnesium is introduced to the zeolite at the hydrogel stage as opposed to either the addition after the hydrogel has been dried and calcined or to the zeolite prior to addition to the alumina hydrosol. It is believed that the zeolite in the hydrogel is more readily susceptible to ion exchange with magnesium. It is also believed that having pseudo-boehmite present, as opposed to gamma-alumina, during contacting with the magnesium solution greatly reduces the possibility that the magnesium will ion exchange with the alumina matrix. Thus, a more efficient use of magnesium is obtained by following the method of the instant invention. The amount of magnesium-containing zeolite may range from 1 to 50 wt. % based on the weight of the finished catalyst composite. Preferably, the amount of magnesium-containing zeolite ranges from 5 to 25 wt. % of the finished catalyst.

Any suitable magnesium compound may be used to introduce the magnesium cation into the zeolite. Representative magnesium compounds include magnesium nitrate, magnesium benzoate, magnesium propionate, magnesium 2-ethylhexoate, magnesium carbonate, magnesium formate, magnesium oxalate, magnesium amide, magnesium bromide, magnesium chloride, magnesium acetate, magnesium lactate, magnesium laurate, magnesium oleate, magnesium palmitate, magnesium silicylate, magnesium stearate, and magnesium sulfide. It is preferred that the magnesium compound be in solution in order to facilitate the contact with the hydrogel. Any solvent relatively inert to the hydrogel and the magnesium compound may be employed. Suitable solvents include water and aliphatic, aromatic, or alcoholic liquids.

Contacting the magnesium-containing solution with the hydrogel is carried out at a temperature from 0° to 150° C. The preferred temperature range is from about 25° to 100° C. The preferred time of contact can vary from about 1 to 24 hours, with some advantage being possible with very short contact times greater than 10 minutes. The physical means for contacting the magnesium-containing solution with hydrogel can be accomplished by a plurality of methods, with no one method having a particular advantage. Such contacting methods may include, for example, a stationary bed of hydrogel particles in an agitated solution, a stationary bed of hydrogel particles in a continuously flowing solution, a stationary bed of hydrogel particles in a static solution or any other means which efficiently contacts the magnesium-containing solution with the hydrogel comprising the pseudo-boehmite and zeolite.

The amount of magnesium incorporated into the zeolite should be such that greater than 50% of the available ion exchange sites are occupied. The amount of magnesium may range from 0.1 wt. % of the finished catalyst to as high as 10 wt. %. By "finished catalyst", it is meant the final catalyst formulation suitable for contact with the hydrocarbon feed. Preferably, the amount of magnesium present in the finished catalyst composition is between 0.5 and 5 wt. %.

It is contemplated that other metals may be directly substituted into the catalyst in place of magnesium if desired by use of the same methods as described herein. Such alternative metals include calcium, lanthanum, and copper or mixtures of these metals.

The catalyst of the instant invention also contains at least one Group VIII metal component. Preferably, this Group VIII metal is selected from the platinum group metals. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum group component exists in the elemental state. The platinum group component generally comprises from about 0.01 to about 2 wt. of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined hydrogel material. For example, the platinum group component may be added to the calcined hydrogel by commingling the calcined hydrogel with an aqueous solution of chloroplatinic or chloropalladic acid. An acid such as hydrogen chloride is generally added to the impregnation solution to aid in the distribution of the platinum group component through the calcined hydrogel particles.

After addition of the Group VIII metal component, the calcined hydrogel comprising gamma-alumina, magnesium-containing zeolite, and platinum is dried at a temperature ranging from about 100° to about 320° C. for a period of at least 2 to about 24 hours or more, and finally calcined or oxidized at a temperature ranging from about 450° to about 650° C. in air or oxygen atmosphere for a period of about 0.5 to about 10 hours in order to convert all of the metallic components to the corresponding oxide form. The resultant oxidative composite is preferably subjected to a substantially water-free reduction step prior to its use in the isomerization of hydrocarbons. This step is designed to selectively reduce the platinum group component to the elemental metallic state, while maintaining the magnesium component in a positive oxidation state, and to ensure a uniform and finely divided dispersion of the metallic components throughout the catalyst. Preferably, a substantially pure and dry hydrogen stream (i.e. less than 20 vol. ppm $H_2O$) is used as the reducing agent in this step. The reducing agent is contacted with the oxidized catalyst at conditions including a reduction temperature ranging from about 200 to about 650° C. and a period of time of about 0.5 to 10 hours effective to reduce substantially all of the platinum group component to the elemental metallic state.

The resulting reduced catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 593° C. or more. It is generally a good practice to perform this presulfiding step operation under substantially water-free conditions.

The following example is presented for purpose of illustration only and is not intended to limit the scope of the present invention.

EXAMPLE

This example presents the results from four different tests. Each test was performed using a pilot plant reactor processing a non-equilibrium $C_8$ aromatic feed comprising 52.2 wt. % meta-xylene, 18.7 wt. % orthoxylene, 0.1 wt. % para-xylene, 21.3 wt.% ethylbenzene, and 0.1 wt. % toluene, with the balance being nonaromatic hydrocarbons. This feed was contacted with 100 cc of catalyst at a liquid hourly space velocity of 2, and a hydrogen to hydrocarbon mole ratio of 4. Reactor pressure and temperature were adjusted to cover a range of conversion values in order to develop the relationship between $C_8$ ring loss and approach to xylene equilibrium (as determined by product para-xylene to total xylene weight ratio). At the same time, at each temperature, the pressure was chosen to maintain a constant mole ratio of $C_8$ naphthenes to $C_8$ aromatics of approximately 0.06.

Initial catalyst preparation for each of the tests described hereinbelow proceeded as follows. A first solution was prepared by adding a zeolite to enough alumina hydrosol, prepared by digesting metallic aluminum in hydrochloric acid, to yield a zeolite content in the finished catalyst equal to about 10 wt. %. As described hereinbelow, the zeolite was either a mordenite or a pentasil. To this first solution is added a second solution of hexamethylenetetramine (HMT). These two solutions were mixed to form a homogeneous admixture which was then dispersed as droplets into an oil bath at a temperature of about 95° C. The droplets remained in the oil bath until they set and formed hydrogel spheres. The spheres were removed from the oil bath and washed with an aqueous solution containing about 0.5 wt. % ammonia. At this point in the preparation the hydrogel spheres which are commonly referred to as "wet hopper spheres" (WHS), were either directly dried and calcined or contacted with a magnesium-containing solution.

The first test, designated as Run A, which is in accordance with the invention, utilized a catalyst wherein the zeolite contained in the hydrogel was sodium form mordenite. A stationary bed of WHS, comprising the mordenite and pseudo-boehmite alumina, was contacted with an aqueous solution of 1.5 molal magnesium acetate by continuously circulating the solution at a rate of about 8 ml/minute. The temperature of the magnesium acetate solution was maintained at about 94° C. for a period of about 20 hours. A deionized water wash using about 10 bed volumes was performed at the conclusion of the magnesium addition step. The WHS were then air dried at 110° C. for about 12 hours and then calcined in air at a temperature of about 6500° C.

The calcined WHS were then impregnated with a solution of chloroplatinic acid, containing 2 wt. % hydrochloric acid (based on calcined WHS), to yield a final platinum content of 0.28 wt. %. The impregnated spheres were oxidized and chloride adjusted at 525° C., reduced in an environment of $H_2$ at 565° C., and sulfided with $H_2S$. The amount of magnesium-containing zeolite was about 9.8 wt. %, the magnesium content was 1.02 wt. %, and the sulfur content was 0.12 wt. %. The isomerization performance results from Run A are presented in FIG. 1.

Run B was also performed in accordance with the instant invention. The test of Run B was essentially identical to that of Run A except the zeolite added to the alumina hydrosol comprised a hydrogen form ZSM-5 zeolite having a silica to alumina mole ratio of 42. The platinum and magnesium contents of this catalyst were 0.32 wt. % and 0.95 wt. %, respectively. The sulfur content was targeted to be 11 wt. %. The isomerization performance results for Run B are also presented in FIG. 1.

To demonstrate the superior performance of the catalyst of the instant invention, two control tests were run. The first test, designated Run C and not in accordance with the instant invention, utilized a catalyst formulation that was prepared identically to the catalysts in Runs A and B, however, in Run C, there was no addition of magnesium to the zeolite. The zeolite used in Run C was the same sodium form mordenite used in Run A. The finished catalyst was analyzed for both platinum and magnesium. The platinum content was 0.32 wt. %, the magnesium content was less than 0.05 wt. %, and the sulfur content was 0.08 wt.%. Test results comparing the isomerization performance of Run C with Runs A and B are presented in FIG. 1.

The second control test, designated as Run D, also not in accordance with the invention, was performed to demonstrate the importance of the means by which magnesium is added to the zeolite. The catalyst used in Run D was prepared in an identical manner as the catalyst of Run A except the magnesium acetate was impregnated onto the catalyst at 25° C. after the WHS had been dried and calcined but prior to platinum addition. Thus the magnesium-containing solution was contacted with calcined spheres comprising gamma-alumina and mordenite. The platinum and magnesium levels were 0.30 wt. % and 0.57 wt. %, respectively. The sulfur content was 0.09 wt. %. In order to accurately access the performance of this second control process, in particular, in order to conduct a comparison at the same Mg levels, it was necessary to prepare another catalyst in accordance with the instant invention following the procedure used for the catalyst of Run A. In preparing this catalyst, a temperature of 25° C. was maintained during the contact of the WHS with the magnesium acetate solution. The platinum content was 0.3 wt. %, the magnesium content was 0.56 wt. %, and the sulfur content was 0.02 wt. %. This catalyst was tested as Run E. A comparison of results for Run D, not of the invention, and Run E, in accordance with the invention, is graphically depicted in FIG. 2.

Figure 2:
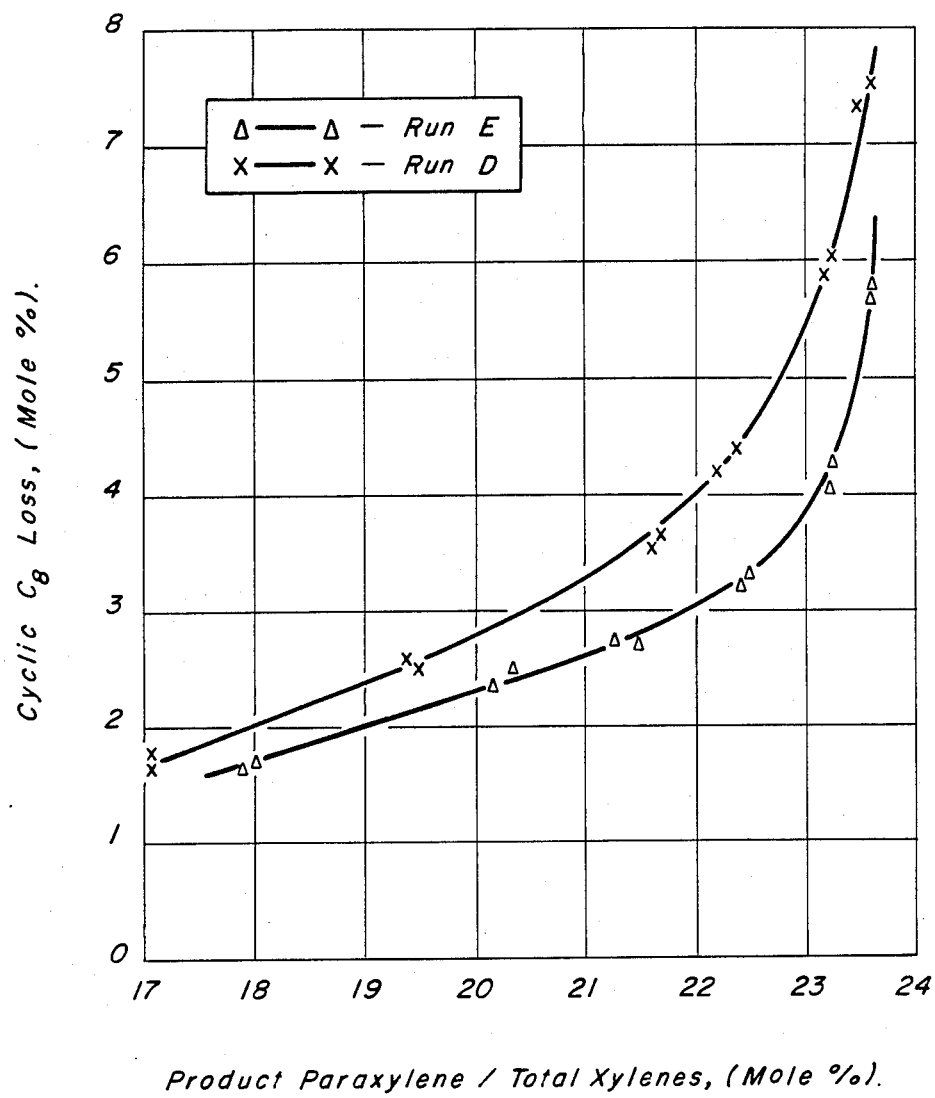
FIG. 2 represents the performance of a catalyst E of the invention, but having a higher magnesium content, and control catalyst D having magnesium added by a different procedure.

Both FIGS. 1 and 2 graphically illustrate the same performance parameters. The x-axis is the concentration of para-xylene in the product, expressed as mole % relative to the total xylenes in the product. The y-axis represents the amount of $C_8$ cyclic hydrocarbons lost due to side reactions. This parameter is defined as the sum of $C_8$ aromatics and naphthenes in the feed minus the amount of $C_8$ aromatics and naphthenes in the product divided by the $C_8$ aromatic and naphthenes in the feed.

The isomerization performance results presented in both FIGS. 1 and 2 clearly indicate the advantage of the instant invention. More specifically, if the results of using a catalyst of the instant invention is compared to those of the control runs, while operating at conditions to produce a product containing 22 mole percent para-xylene, about 25% less $C_8$ aromatic hydrocarbons are lost due to side reactions.

What is claimed:

1. An isomerization catalyst comprising an alumina matrix, at least one Group VIII metal component, and 1 to 50 wt. % of a magnesium-containing zeolite, wherein the zeolite is either mordenite or a pentasil, and the magnesium-containing zeolite is prepared from a hydrogel comprising pseudo-boehmite alumina and the zeolite, with the hydrogel having been contacted with an aqueous magnesium solution.

2. The catalyst of claim 1 wherein the catalyst is spherical in shape and contains between 50 and 99 wt. % gamma-alumina.

3. The catalyst of claim 1 wherein the catalyst contains between 0.1 and 5 wt. % platinum.

4. The catalyst of claim 1 wherein the magnesium-containing zeolite is a pentasil selected from the group consisting of ZSM-5, ZSM-8, ZSM-11, ZSM-12, ZSM-23, and ZSM-35 zeolites.

5. The catalyst of claim 4 wherein the magnesium-containing pentasil is a gallosilicate.

6. The catalyst of claim 1 wherein the catalyst contains an amount of magnesium equal to at least 50% of the exchange capacity of the zeolite.

7. A xylene isomerization catalyst which contains 0.2-2.0 wt. % magnesium and consists essentially of an alumina matrix, at least one Group VIII metal component, to 50 wt. % of a magnesium-containing zeolite, wherein the magnesium containing zeolite is prepared by contacting a hydrogel comprising pseudo-boehmite alumina and zeolite with an aqueous magnesium solution.

8. The catalyst of claim 7 wherein the catalyst is spherical in shape and contains between 50 and 99 wt. % gamma-alumina.

9. The catalyst of claim 7 wherein the catalyst contains between 0.1 and 5 wt. % platinum.

10. The catalyst of claim 7 wherein the zeolite is mordenite.

11. The catalyst of claim 7 wherein the zeolite is a pentasil selected from the group consisting of ZSM-5, ZSM-8, ZSM-11, ZSM-12, ZSM-23, and ZSM-35 zeolites.

12. The catalyst of claim 11 wherein the pentasil is a gallosilicate.

13. The catalyst of claim 7 wherein the aqueous magnesium solution is contacted with the hydrogel at a temperature ranging from 25° to 100° C. for 1 to 24 hours.

14. The catalyst of claim 13 wherein after contacting with the aqueous magnesium solution, the hydrogel is dried at a temperature of from 50° to 200° C. and calcined to convert the pseudo-boehmite alumina to essentially gamma-alumina prior to addition of the Group VIII metal component.

15. The catalyst of claim 14 wherein the hydrogel is prepared by the oil drop method.

16. A catalyst for the isomerization of xylenes present in a feed stream comprising a non-equilibrium mixture of xylenes containing ethylbenzene, the catalyst containing 0.2-2.0 wt. % magnesium and consisting essentially of 75 to 95 wt. % gamma-alumina, 0.1 to 5 wt. % platinum, and 5 to 25 wt. % magnesium-containing mordenite, which catalyst is prepared by:
    (a) contacting an uncalcined hydrogel prepared by the oil drop method and comprising pseudo-boehmite and mordenite with an aqueous magnesium solution at a temperature of from 25° to 100° C. for 1 to 24 hours;
    (b) drying and calcining the resultant hydrogel to convert the pseudo-boehmite alumina to essentially gamma-alumina: and,
    (c) impregnating the calcined hydrogel with platinum.

17. A method of manufacturing an isomerization catalyst which comprises the steps of:
    (a) contacting an uncalcined hydrogel comprising pseudo-boehmite and a zeolite with an aqueous magnesium solution at a temperature of from 25° to 100° C. for 1 to 24 hours;
    (b) drying and calcining the resultant hydrogel to convert the pseudo-boehmite alumina to essentially gamma-alumina; and,
    (c) impregnating the calcined hydrogel with platinum.

18. The method of claim 17 wherein the zeolite is mordenite.

19. The method of claim 17 wherein the zeolite is a pentasil selected from the group consisting of ZSM-5, ZSM-8, ZSM-11, ZSM-12, ZSM-23, and ZSM-35 zeolites.

20. The method of claim 17 wherein after contacting with the aqueous magnesium solution, the hydrogel is dried at a temperature of from 50° to 200° C. and calcined to convert the pseudo-boehmite alumina to essentially gamma-alumina followed by addition of the Group VIII metal component.

21. The method of claim 20 further characterized in that the catalyst contains 0.2-2.0 wt. % magnesium and consists essentially of 75 to 95 wt. % gamma-alumina, 0.1 to 5 wt. % platinum, and 5 to 25 wt. % magnesium-containing mordenite.

* * * * *